United States Patent [19]
Hasan et al.

[11] Patent Number: 6,107,466
[45] Date of Patent: Aug. 22, 2000

[54] ACCELERATION OF WOUND HEALING BY PHOTODYNAMIC THERAPY

[75] Inventors: Tayyaba Hasan, Arlington; Michael R. Hamblin, Revere, both of Mass.; Kenneth Trauner, Sacramento, Calif.

[73] Assignee: The General Hospital Corporation, Boston, Mass.

[21] Appl. No.: 09/160,528

[22] Filed: Sep. 24, 1998

Related U.S. Application Data

[63] Continuation-in-part of application No. 08/741,816, Oct. 31, 1996.
[60] Provisional application No. 60/026,315, Sep. 19, 1996.
[51] Int. Cl.$^7$ ........................................... A61N 1/30
[52] U.S. Cl. ........................... 530/351; 530/399; 604/20; 607/88; 607/89
[58] Field of Search .................................. 530/351, 399; 604/20; 607/88, 89

[56] References Cited

U.S. PATENT DOCUMENTS

| | | | |
|---|---|---|---|
| 5,368,841 | 11/1994 | Trauner et al. | 424/9 |
| 5,405,369 | 4/1995 | Selman et al. | 607/88 |

OTHER PUBLICATIONS

Arm et al., "Effect of Controlled Release of Platelet–derived Growth Factor From a Porous Hydroxyapatite Implant on Bone Ingrowth", Biomaterials 17:703–709, 1996.
Bachor et al., "Mechanism of Photosensitization by Microsphere–bound Chlorin $e_6$ in Human Bladder Carcinoma Cells", Cancer Research 51:4410–4414, 1991.
Bachor et al., "Photosensitized Destruction of Human Bladder Carcinoma Cells Treated with Chlorin $e_6$–Conjugated Microspheres", Proc. Natl. Acad. Sci. USA 88:1580–1584, 1991.
Batlle, "Porphyrins, Poprhyrias, Cancer and Photodynamic Therapy –A Model for Carcinogenesis", J. Photochem. Photobiol. B: Biol. 20:5–22, 1993.
Beck et al., "One Systemic Administration of Transforming Growth Factor–β1 Reverses Age— or Glucocorticoid–impaired Wound Healing", J. Clin. Invest. 92:2841–2849, 1993.
Beems et al., "Photosensitizing Properties of Bacteriochlorophyllin αand Bacteriochlorin α, Two Derivatives of Bacteriochlorophyll α", Photochemistry and Photobiology 46:639–643, 1987.
Bennett et al., "Growth Factors and Wound Healing: Biochemical Properties of Growth Factors and Their Receptors", The American Journal of Surgery 165:728–737, 1993.
Brown et al., "Acceleration of Tensile Strength of Incisions Treated with EGF and TGF–β", Ann. Surg. 208:788–794, 1988.
Cox, "Transforming Growth Factor–Beta 3", Cell Biology International 19:357–371, 1995.
Davies et al., "In Vitro Assessment of the Biological Activity of Basic Fibroblast Growth Factor Released from Various Polymers and Biomatrices", Journal of Biomaterials Applications 12:31–56, 1997.
Detmar et al., "Keratinocyte–Derived Vascular Permeability Factor (Vascular Endothelial Growth Factor) is A Potent Mitogen for Dermal Microvascular Endothelial Cells", J. Investigative Dermatology 105:44–50, 1995.
Dougherty et al., Photodynamic Therapy of Neoplastic Disease, vol. 1, pp. 1–19, CRC Press, (Kessel, ed.) Boca Raton, 1989.
Evans et al., "Effect of Photodynamic Therapy on Tumor Necrosis Factor Production by Murine Macrophages", Journal of the National Cancer Institute 82:34–39, 1990.
Frank et al., "Regulation of Vascular Endothelial Growth Factor Expression in Cultured Keratinocytes", The Journal of Biological Chemistry 270: 12607–12613, 1995.
Fukunaga et al., "Aluminium β–Cyclodextrin Sulphate as a Stabilizer and Sustained–release Carrier for Basic Fibroblast Growth Factor", J. Pharm. Pharmacol. 46:168–171, 1994.
Greenhalgh, "The Role of Growth Factors in Wound Healing", The Journal of Trauma: Injury, Infection, and Critical Care 41:159–167, 1996.
Gurinovich et al., "Photodynamic Activity of Chlorin $e_6$ and Chlorin $e_6$ Ethylenediamide In Vitro and In Vivo", J. Photochem. Photobiol. B: Biol. 13:51–57, 1992.
Hamblin et al., "Photosensitizer Targeting in Photodynamic Therapy I. Conjugates of Haematoporphyrin With Albumin and Transferrin", Journal of Photochemistry and Photobiology B: Biology 26:45–56, 1994.
Hamblin et al., "Photosensitizer Targeting in Photodynamic Therapy II. Conjugates of Haematoporphyrin With Serum Lipoproteins", Journal of Photochemistry and Photobiology B: Biology 26: 147–157, 1994.
Hill et al., "The Effect of PDGF on the Healing of Full Thickness Wounds in Hairless Guinea Pigs", Comp. Biochem. Physiol. 100A:365–370, 1991.
Kamler et al., "Impact of Ischemia in Tissue Oxygenation and Wound Healing: Improvement By Vasoactive Medication", Adv. Exp. Med. Biol. 316:419–424, 1992.
Kessel, "Determinants of Photosensitization by Purpurins", Photochemistry and Photobiology 50:169–174, 1989.
Kessel, "Interactions Between Porphyrins and Mitochondrial Benzodiazepine Receptors", Cancer Letters 39:193–198, 1988.
Kessel et al., "Photosensitization with Derivatives of Chlorophyll", Photochem. & Photobiology 49:157–160, 1989.
Kiecolt–Glaser et al., "Slowing of Wound Healing by Psychological Stress", Lancet 346:1194–196, 1995.

(List continued on next page.)

Primary Examiner—Cecilia J. Tsang
Assistant Examiner—Patrick R. Delaney
Attorney, Agent, or Firm—Fish & Richardson P.C.

[57] ABSTRACT

Disclosed is a method for accelerating wound healing in a mammal. The method includes identifying an unhealed wound site or partially-healed wound site in a mammal; administering a photosensitizer to the mammal; waiting for a time period wherein the photosensitizer reaches an effective tissue concentration at the wound site; and photoactivating the photosensitizer at the wound site. The dose of photodynamic therapy is selected to stimulate the production of one or more growth factor by cells at the wound site, without causing tissue destruction.

17 Claims, 1 Drawing Sheet

OTHER PUBLICATIONS

Koren et al., "Photodynamic Therapy–An Alternative Pathway in the Treatment of Recurrent Breast Cancer", Int. J. Radiation Oncology Biol. Phys. 28:463–466, 1993.

Kreimer–Birnbaum, "Modified Porphyrins, Chlorins, Phthalocyanines, and Purpurins: Second–Generation Photosensitizers for Photodynamic Therapy", Seminars in Hematology 26:157–173, 1989.

Kusstatscher et al., "Different Molecular Forms of Basic Fibroblast Growth Factor (bfGF) Accelerate Duodenal Ulcer Healing in Rats", The Journal of Pharmacology and Experimental Therapeutics 275:456–461, 1995.

Molpus et al., "Intraperitoneal Photodynamic Therapy of Human Epithelial Ovarian Carcinomatosis in a Xenograft Murine Model", Cancer Research 56:1075–1082, 1996.

Morgan et al., "Metallopurpurins and Light: Effect on Transplantable Rat Bladder Tumors and Murine Skin", Photochemistry and Photobiology 51:589–592, 1990.

Nicoll et al., "In Vitro Release Kinetics of Biologically Active Transforming Growth Factor–β1 from a Novel Porous Glass Carrier", Biomaterials 18:853–859, 1997.

Obochi et al., "Photodynamic Therapy (PDT) as a Biological Modifier", SPIE 2675:122–131, 1996.

Puolakkainen et al., "The Enhancement in Wound Healing by Transforming Growth Factor–$\beta_1$ (TGB–$B_1$) Depends on the Topical Delivery System", Journal of Surgical Research 58:321–329, 1995.

Reed et al., "Wound Repair in Older Patients: Preventing Problems and Managing the Healing", Geriatrics 53:88–94, 1998.

Rosenberg, "Wound Healing in the Patient with Diabetes Mellitus", Nursing Clinics of North America 25:247–261, 1990.

Suh et al., "Insulin–Like Growth Factor–I Reverses the Impairment of Wound Healing Induced by Corticosteroids in Rats", Endocrinology 131:2399–2403, 1992.

Uthoff et al., "Thalidomide as Replacement for Steroids in Immunosuppression After Lung Transplantation", Ann. Thorac. Surg. 59:277–282, 1995.

Yamamoto et al., "Activation of Mouse Macrophages by In Vivo and In Vitro Treatment With a Cyanine Dye, Lumin", J. Photochem. Photobiol. B: Biol. 13:295–306, 1992.

Yamamoto et al., "Effectiveness of Photofrin II in Activation of Macrophages and In Vitro Killing of Retinoblastoma Cells", Photochemistry and Photobiology 60:160–164, 1994.

Young, "Nutritional Problems in Critical Care Malnutrition and Wound Healing", Heart & Lung 17:60–67, 1988.

ACCELERATION OF WOUND HEALING BY PHOTODYNAMIC THERAPY

CROSS REFERENCE TO RELATED APPLICATIONS

This application is a continuation-in-part of copending application Ser. No. 08/741,816, filed Oct. 31, 1996, which claims benefit from provisional application Ser. No. 60/026,315, filed Sep. 19, 1996, now abandoned.

FIELD OF THE INVENTION

This invention relates to cell biology, medicine, wound healing and photodynamic therapy.

BACKGROUND OF THE INVENTION

Delayed or impaired wound healing can result from various conditions. These include diabetes (Rosenberg (1990) *Nurs. Clin. North Am.* 25:247–261), peripheral vascular disease (Kamler et al. (1992) *Adv. Exp. Med. Biol.* 316:419–424), advanced age (Reed (1998) *Geriatrics* 53:88–94), malnutrition (Young (1988) *Heart Lung* 17:60–67), immune suppression and corticosteroid use (Uthoff et al. (1995) *Ann. Thorac. Surg.* 59:277–282), psychological stress (Kiecolt-Glaser et al. (1995) *Lancet* 346:1194–1196), and cancer radiotherapy and chemotherapy (Mason et al. (1992) *Clin. Oncol.* 4:32–35). There is presently no standard therapy for delayed or impaired wound healing other than supportive care.

The initiation and control of concerted processes responsible for wound healing are governed by polypeptide molecules known as growth factors (Bennett et al. (1993) *Review, Am. J. Surg.* 165:728–737). These polypeptides can be categorized by sequence homology or by function.

Based on sequence homology, growth factor family groups include epidermal growth factor family (EGF) (Brown et al. (1988) *Ann. Surg.* 208:788–794), platelet derived growth factor family (PDGF) (Hill et al. (1991) *Comp. Biochem. Physiol A.* 100:365–370), insulin-like growth factor family (IGF) (Suh et al. (1992) *Endocrinology* 131:2399–2403), transforming growth factor-beta family (TGF-3) (Cox (1995) *Cell Biol. Int.* 19:357–371), fibroblast growth factor family (FGF) (Kusstatscher et al. (1995) *J. Pharmacol. Exp. Ther.* 275:456–461), vascular endothelial growth factor family (VEGF) (Frank et al. (1995) *J. Biol. Chem.* 270:12607–12613).

Growth factors can be grouped functionally, according to the role they play in initiating and controlling the various phases of wound healing. A first group consists of chemotactic growth factors, i.e., those that attract inflammatory cells such as monocyte/macrophage and fibroblasts to the cell site. A second group consists of growth factors that act as mitogens to stimulate cellular proliferation. A third group consists of that growth factors that stimulate angiogenesis. A fourth group consists of growth factors that affect the production and degradation of the extracellular matrix. A fifth group of growth factors consists of those that influence the synthesis of cytokines and growth factors of neighboring cells.

Growth factors constitute a subclass of cytokines. Growth factors are distinguished from other cytokine subclasses by their ability to act as mitogens, chemoattractants and proliferation inducers on cells of epithelial, endothelial, and mesenchymal origins. In particular, the pleiotropic growth factor TGF-$\beta$ is important in orchestrating the wound healing response (Beck et al. (1993) *J. Clin. Invest.* 92:2841–2849).

Exogenously applied growth factors (particularly BFGF, PDGF, EGF, and TGF-B) have been used to stimulate wound healing (Puolakkainen et al. (1995) *J. Surg. Res.* 58:321–329; Greenhalgh et al. (1996) *J. Trauma* 41:159–167). A difficulty in using this approach has been in formulating the growth factors in such a way as to ensure their sustained slow release in a biologically active form (Davies et al. (1997) *J. Biomater. Appl.* 12:31–56; Nicoll et al. (1997) *Biomaterials* 18:853–859; Arm et al. (1996) *Biomaterials* 17:703–709; and Fukunaga et al. (1994) *J. Pharm. Pharmacol.* 46:168–171).

SUMMARY OF THE INVENTION

It has been discovered that low doses of photodynamic therapy (PDT) upregulate the expression and/or secretion of growth factors involved in wound healing. One effect is an increase in wound breaking strength in vivo.

Based on this discovery, the invention features a method for accelerating the healing of a wound in a mammal. The method includes: (a) identifying an unhealed wound site or partially-healed wound site in a mammal; (b) administering a therapeutically effective amount of a photosensitizer to the mammal; (c) waiting for a time period wherein the photosensitizer reaches an effective tissue concentration at the wound site; (d) photoactivating the photosensitizer at the wound site by delivering specifically to the wound site light of an effective wavelength and intensity, for an effective duration, thereby delivering a therapeutically effective dose of PDT. The therapeutically effective dose of PDT accelerates wound healing by stimulating the biosynthesis and/or secretion of one or more growth factors by cells at the wound site, without causing tissue destruction.

The cells producing the growth factor in response to the PDT can be fibroblast cells, myofibroblast cells, macrophage cells, endothelial cells, epithelial cells, or other cell types at the wound site. Examples of growth factors whose production may be stimulated by the PDT include PDGF, TGF-$\beta$, $\alpha$-FGF, $\beta$-FGF, TGF-$\alpha$, EGF, IGF, VEGF, KGF, and HGF.

Various types of molecules can be used as the photosensitizer, e.g., porphyrins, chlorins, bacteriochlorins, purpurins, phthalocyanines, naphthalocyanines, texaphyrins, and non-tetrapyrroles. Specific examples of photosensitizers are photofrin, benzoporphyrin derivative, tin etiopurpurin, sulphonated chloroaluminium phthalocyanine and methylene blue. The photosensitizer can be conjugated to another molecule or can be unconjugated. The photosensitizer can be in the form of a macromolecular conjugate. A preferred macromolecular conjugate is polylysine chlorin-e6 conjugate.

In some embodiments of the invention, the photosensitizer localizes to a particular cell type or to an organelle in a cell at the wound site. The photosensitizer can be targeted to a particular cell type or to an organelle. Targeting can be achieved by conjugation of the photosensitizer to a targeting moiety, e.g., a polypeptide or microparticle.

Administration of the photosensitizer can be local or systemic. Systemic administration can be oral or parenteral. For systemic administration, dosage can be between about 0.1 mg/kg and about 50 mg/kg. Preferably, the dosage is between about 0.5 mg/kg and about 10 mg/kg. Local administration can be topical or by injection, at or near the wound site.

Photoactivating light can be delivered to the wound site from a conventional light source or from a laser. Delivery can be direct, by transillumination, or by optical fiber.

As used herein, "photoactivation" means a light-induced chemical reaction of a photosensitizer which produces a biological effect.

As used herein, "photosensitizer" means a chemical compound that produces a biological effect upon photoactivation or a biological precursor of a compound that produces a biological effect upon photoactivation.

As used herein, "without tissue destruction" means without formation of non-viable tissue as a result of necrosis or apoptosis leading to eschar formation and/or sloughing.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

DETAILED DESCRIPTION

Wounds

Figure 1:
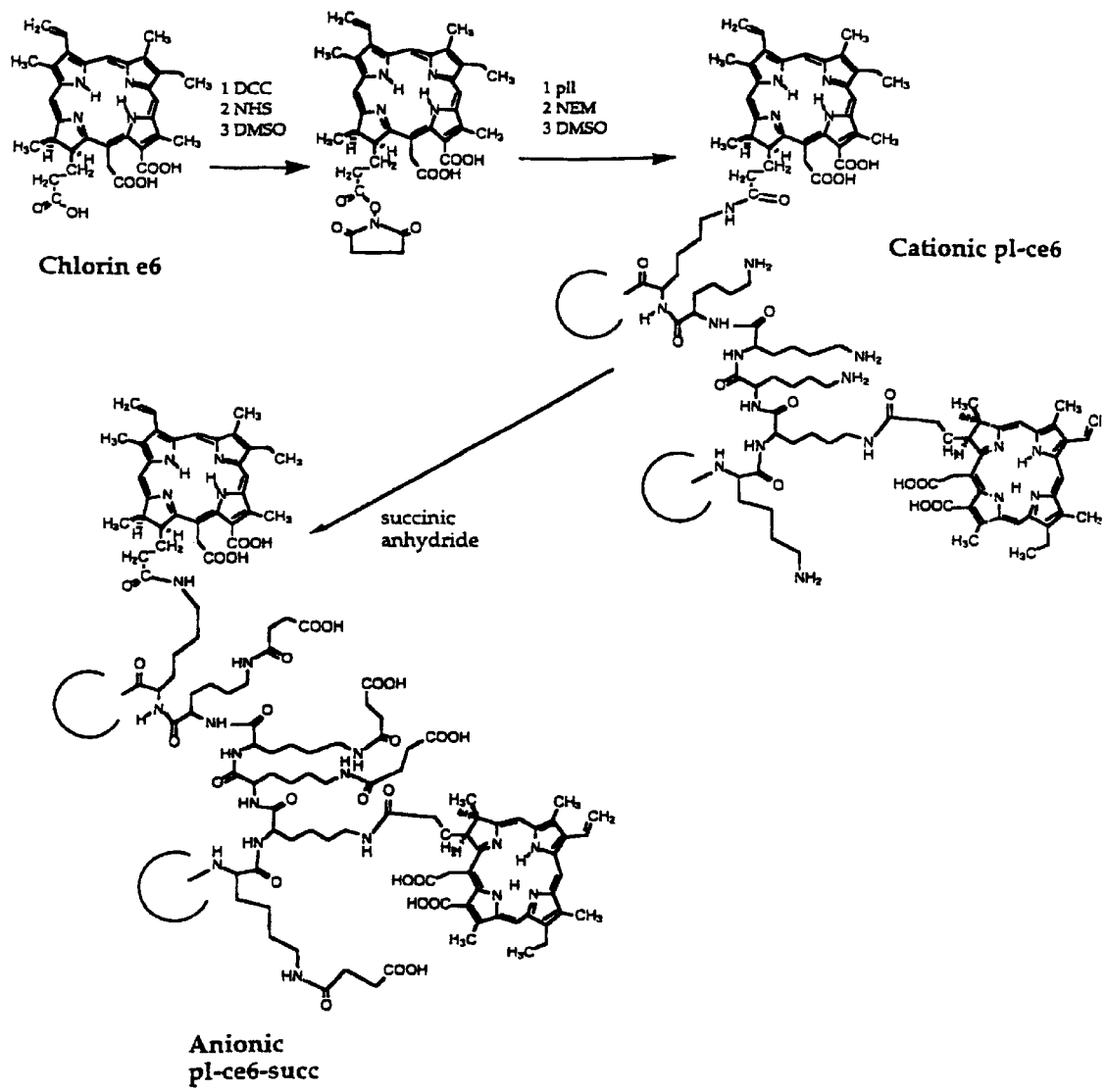
FIG. 1 is a diagram illustrating steps in the preparation of a cationic and anionic polylysine chlorin-e6 conjugate.

The present invention involves identifying an unhealed wound or a partially-healed wound in a mammal, e.g., a human. The wound can be a non-penetrating wound, or a penetrating wound. Examples of wounds that can be treated by the method of this invention include abrasions, lacerations, surgical incisions, and burns.

The invention is particularly useful where normal healing processes are impaired, retarded or suppressed. This can occur due to conditions such as diabetes, peripheral vascular disease, immune suppression, corticosteroid use, cancer radiotherapy, and cancer chemotherapy.

Photosensitizer

The photosensitizer is a chemical compound that produces a biological effect upon photoactivation, or a biological precursor of a compound that produces a biological effect upon photoactivation. The photosensitizer must have a sufficiently low toxicity to permit administration to the patient with a medically acceptable level of safety. Preferably, the photosensitizer is essentially nontoxic upon photoactivation.

Various photosensitizers are known and can be used in the practice of this invention. Preferably, the photosensitizer used is not a photosensitizer that inactivates growth factor activity, e.g., CASPc (a phthalocyanine). Photosensitizers typically have chemical structures that include multiple conjugated rings that allow for light absorption and photoactivation. They differ in the properties of light absorption and fluorescence, biodistribution, temporal uptake, clearance, and mechanisms of photoactivatable cytotoxicity. Classes of photosensitizer include hematoporphyrins (Batlle (1993) *J. Photochem. Photobiol. Biol.* 20:5–22; Kessel (1988) *Cancer Let.* 39:193–198), uroporphyrins, phthalocyanines (Kreimer-Birnbaum, (1989) *Seminars in Hematology* 26:157–173), purpurins (Morgan et al. (1990) *Photochem. Photobiol.* 51:589–592; Kessel, (1989) *Photochem. Photobiol.* 50:169–174), acridine dyes, bacteriochlorophylls (Beems et al. (1987) *Photochem. Photobiol.* 46:639–643; Kessel et al. (1989) *Photochem. Photobiol.* 49:157–160), and bacteriochlorins (Gurinovich et al. (1992) *J. Photochem. Photobiol. Biol.* 13:51–57). Specific examples of suitable photosensitizer are listed below.

Photosensitizer

1. Photofrin®
2. Synthetic diporphyrins and dichlorins
3. Hydroporphyrins, e.g., chlorins and bacteriochlorins of the tetra(hydroxyphenyl) porphyrin series
4. phthalocyanines
5. O-substituted tetraphenyl porphyrins (picket fence porphyrins)
6. 3,1-meso tetrakis (o-propionamido phenyl) porphyrin
7. Verdins
8. Purpurins, e.g., tin and zinc derivatives of octaethylpurpurin (NT2), and etiopurpurin (ET2)
9. Chlorins, e.g., chlorin-e6, and mono-l-aspartyl derivative of chlorin-e6
10. Benzoporphyrin derivatives (BPD), e.g., benzoporphyrin monoacid derivatives, tetracyanoethylene adducts of benzoporphyrin, dimethyl acetylenedicarboxylate adducts of benzoporphyrin, Diels-Adler adducts, and monoacid ring "a" derivative of benzoporphyrin
11. Low density lipoprotein mediated localization parameters similar to those observed with hematoporphyrin derivative (HPD)
12. sulfonated aluminum phthalocyanine (Pc) sulfonated AlPc disulfonated ($AlPcS_2$) tetrasulfonated derivative sulfonated aluminum naphthalocyanines chloroaluminum sulfonated phthalocyanine (CASP)
13. zinc naphthalocyanines
14. anthracenediones
15. anthrapyrazoles
16. aminoanthraquinone
17. phenoxazine dyes
18. phenothiazine derivatives
19. chalcogenapyrylium dyes cationic selena and tellurapyrylium derivatives
20. ring-substituted cationic PC
21. pheophorbide α
22. hematoporphyrin (HP)
23. protoporphyrin
24. 5-amino levulinic acid The photosensitizer can be any of various types of compounds, including porphyrins, chlorins, bacteriochlorins, purpurins, phthalocyanines, naphthalocyanines, texaphyrines, and non-tetrapyrrole photosensitizer. Specific examples of photosensitizers are Photofrin, benzoporphyrin derivative, tin etiopurpurin, sulfonated chloroaluminum phthalocyanine, methylene blue, and chlorin-e6.

Photosensitizer Conjugation, Formulation, and Administration

The photosensitizer can be modified to form a macromolecular conjugate. An exemplary macromolecular conjugate is poly-l-lysine chlorin-e6 conjugate. A macromolecular conjugate can be used to facilitate or promote localization to an intracellular organelle of a cell.

A single photosensitizer compound can be used alone in the practice of this invention. Alternatively, two or more photosensitizer can be used in combination, provided that light of an effective wavelength for each photosensitizer in the combination is used in the photoactivation step.

An alternative to administration of the photosensitizer compound itself, is administration of a photosensitizer precursor molecule. This approach is illustrated by the use of 5-aminolevulinic acid, which causes endogenous production of the photosensitizer protoporphyrin IX (Morgan et al. (1989) *J. Med. Chem.* 32:904–908.

The photosensitizer can be chosen, or chemically modified, to optimize its usefulness in specific treatment situations. For example, the photosensitizer can be chemically modified to reduce its interaction with articular cartilage. This could be done by eliminating a positive charge to reduce association with negatively charged proteoglycans of articular cartilage.

For targeting to a particular organ, tissue, cell type, or organelle the photosensitizer can be chemically conjugated to a targeting moiety. In some embodiments, the photosensitizer is chemically conjugated to a targeting moiety that binds to a cell surface receptor, e.g., a macrophage receptor or an endothelium surface receptor.

Macrophages can be targeted through their phagocytic activity. Such targeting involves conjugating the photosensitizer to a microparticle. A suitable microparticle is a 1 μm polystyrene microsphere (Polysciences, Inc.). Photosensitizer-microparticle conjugates are taken up selectively by macrophages, through their characteristic phagocytic activity. Conjugation of a photosensitizer to a microparticle can be by methods known in the art. See, e.g., Bachor et al. (1991) *Proc. Natl. Acad. Sci. USA* 88:1580–1584.

The photosensitizer can be formulated to optimize its usefulness for particular applications. For example, it can be formulated in a salve or gel for topical application. It can be formulated for parenteral administration or oral administration. Appropriate formulation can be carried out by one of ordinary skill in the art, without undue experimentation.

Administration of the photosensitizer can be local or systemic. The administration can be by any suitable route, including topical, intravenous, intraarticular, subcutaneous, intramuscular, intraventricular, intracapsular, intraspinal, intraperitoneal, topical, intranasal, oral, buccal, rectal or vaginal. The preferred route of administration will depend on the size and nature of the wound, the location of the wound, and the photosensitizer used.

Parenteral formulations may be in the form of liquid solutions or suspensions; for oral administration, formulations may be in the form of tablets or capsules; and for intranasal formulations, in the form of powders, nasal drops, or aerosols.

Methods for making formulations are known in the art. Guidance concerning such methods can be found in standard references such as "Remington's Pharmaceutical Sciences." Formulations for parenteral administration may, for example, contain as excipients sterile water or saline, Cremophor EL, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, liposomes, and antibody conjugates. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

Where the size, nature, and location of the wound renders local administration of the photosensitizer feasible, local administration is preferred over systemic administration. Advantages of local administration include reducing number of side effects, reducing the likelihood of a particular side effect, or both. In addition, local administration generally yields an effective concentration of photosensitizer at the wound site more rapidly, and permits greater control over photosensitizer concentration at the wound site.

Photoactivation

Following administration of the photosensitizer, it is necessary to wait for the photosensitizer to reach an effective tissue concentration at the wound site, before photoactivation. Duration of the waiting step varies, depending on factors such as route of photosensitizer administration, wound location, and speed of photosensitizer movement in the body. Determining a useful range of waiting step duration is within ordinary skill in the art.

Following the waiting step, the photosensitizer is activated by photoactivating light applied to the wound site. This is accomplished by applying light of a suitable wavelength and intensity, for an effective length of time, specifically to the wound site. The suitable wavelength, or range of wavelengths, will depend on the particular photosensitizer (s) used. Wavelength specificity for photoactivation depends on the molecular structure of the photosensitizer. Photoactivation occurs with sub-ablative light doses. Determination of suitable wavelength, light intensity, and duration of illumination is within ordinary skill in the art.

The light for photoactivation can be produced and delivered to the wound site by any suitable means. For superficial wounds or open surgical wounds, suitable light sources include broadband conventional light sources, broad arrays of LEDs, and defocussed laser beams.

For non-superficial wound sites, including those in intracavitary settings, the photoactivating light can be delivered by optical fiber devices. For example, the light can be delivered by optical fibers threaded through small gauge hypodermic needles. Optical fibers also can be passed through arthroscopes. In addition, light can be transmitted by percutaneous instrumentation using optical fibers or cannulated waveguides.

Photoactivation at non-superficial wound sites also can be by transillumination. Some photosensitizers can be activated by near infrared light, which penetrates more deeply into biological tissue than other wavelengths. Thus, near infrared light is advantageous for transillumination. Transillumination can be performed using a variety of devices. The devices can utilize laser or non-laser sources, i.e. lightboxes or convergent light beams.

PDT dosage depends on various factors, including the amount of the photosensitizer administered, the wavelength of the photoactivating light, the intensity of the photoactivating light and the duration of illumination by the photoactivating light. Thus, the dose of PDT can be adjusted to a therapeutically effective dose by adjusting one or more of these factors. Such adjustment is within ordinary skill in the art.

The invention is further illustrated by the following experimental examples. The examples are provided for illustration only, and are not to be construed as limiting the scope or content of the invention in any way.

EXPERIMENTAL EXAMPLES

Poly-l-lysine chlorin-e6 Conjugates

A pair of poly-l-lysine chlorin-e6 (ce6) conjugates possessing opposite charges were made as follows. The ester of ce6 (porphyrin Products, Logan, Utah) was prepared by reacting 1.5 equivalents of dicyclohexylcarbodiimide and 1.5 equivalents of N-hydroxysuccinimide with 1 equivalent of ce6 in dry dimethyl sulfoxide (DMSO). Polylysine hydrobromide (50 mg) (Sigma, St. Louis, Mo.) (average M.Wt. 11000, DP=100) was dissolved in dry DMSO (50 ml) containing N-ethylmorpholine (1 ml), and subsequently added to dry DMSO (1 ml) containing ce6-N-hydroxysuccinimide ester (25 mg). The solution was kept in the dark at room temperature for 24 hours and the resultant ce6 conjugate in the solution had a cationic charge (pl-ce6). The preparation of the anionic ce6 conjugate (pl-ce6-succ) further involved treating the cationic ce6 solution with an excess of succinic anhydride (100 mg dissolved in 0.5 ml dry DMSO) (FIG. 1). The cationic ce6 conjugate-containing solution and the anionic ce6 conjugate-containing solution were dialyzed in DMSO-resistant dialysis membrane with a 3500 MW cutoff (Spectrum Medical Industries, Los Angeles, Calif.) for 24 hours against three changes of 10 mM phosphate buffer (pH7).

The degree of ce6 substitution on the polylysine chains was estimated by measuring the absorbance at 400 nm and calculating the amount of ce6 present using e400nm= 150000. The amount of polylysine was assumed to be the original quantity weighed out. After exhaustive dialysis it was assumed that the remaining ce6 was covalently bound to the polylysine. On each polylysine chain it was estimated that there were 5 ce6 molecules.

Increased Production of TGF-$\beta$ in Keratinocytes

Balb/c murine keratinocytes (Balb/mk) were grown to 60% confluency in P100 dishes in medium containing 10% FBS. The cells were then incubated with different concentrations (0$\mu$M, 0.5$\mu$M and 2$\mu$M) of pl-ce6-succ (d.p. 100, substitution ratio <5%) for 4h. Following incubation of cells with pl-ce6-succ, a fluence (1 Jcm$^{-2}$, 5Jcm$^{-2}$, and 20 Jcm$^{-2}$) of red light from a light emitting diode array centered on 670 nm was delivered to the cells. After 24 hours, cells were lysed and equal amounts of cell protein (25 $\mu$g per lane) from each sample was then loaded on a 15% SDS PAGE gel. Following protein separation by electrophoresis, the gel was electroblotted to a nylon membrane and subsequently probed with anti-TGF-$\beta$ antibody. The bound murine anti TGF-$\beta$ was then detected by a second antibody conjugated to alkaline peroxidase. Cells that were not treated with pl-ce6-succ were used as a control.

Western blot analysis revealed that cells incubated with 0.5 $\mu$M pl-ce6-succ and subsequently exposed to a fluence of 5 Jcm$^{-2}$ showed an increase in TGF-$\beta$ production. No further increase in TGF-$\beta$ production was observed in cells exposed to a fluence of 20 Jcm$^{-2}$.

The largest increase in TGF-$\beta$ production was observed in cells incubated with 2 $\mu$M pl-ce6-succ equivalent and exposed to a fluence of 5 Jcm$^{-2}$. Substantial phytotoxicity to the cells was observed when cells were exposed to a fluence of 20 Jcm$^{-2}$, accounting for the reduced TGF-$\beta$ levels observed.

Increased Production of VEGF in Keratinocytes

Balb/mk, OVCAR-5 and PAM 212 cells were grown to 60% confluency in P100 dishes in medium containing 10% FBS. The cells were then incubated with varying concentrations (0 $\mu$M, 0.5$\mu$M, 2 $\mu$M) of pl-ce6-succ (d.p. 100, substitution ratio <5%) for 4h, and following incubation, a fluence (0 Jcm$^{-2}$, 5 Jcm$^{-2}$, 20 Jcm$^{-2}$) of red light from a light emitting diode array centered on 670 nm was delivered to the cells (see Table 1). After 24 hours, cells were lysed and equal amounts of cell protein (25 $\mu$g per lane) from each sample were then loaded on a 15% SDS PAGE gel. Following protein separation by electrophoresis, the gel was electroblotted to a nylon membrane and subsequently probed with anti VEGF antibody. The bound anti-VEGF antibody was then detected by a second antibody conjugated to alkaline peroxidase.

PAM 212 cells showed a moderate increase in VEGF production in cells exposed to 0.5 $\mu$M ce6 and 5 Jcm$^{-2}$; 0.5 $\mu$M ce6 and 20 Jcm$^{-2}$; and 2 $\mu$M ce6 and 5 Jcm$^{-2}$. A significant increase in VEGF production was observed in cells exposed to 2 $\mu$M pl-ce6-succ and 20 Jcm$^{-2}$.

Balb/mk cells showed a minor increase in VEGF production when treated with 0.5 $\mu$M ce6 and 5 Jcm$^{-2}$; and 0.5 $\mu$M ce6 and 20 Jcm$^{-2}$.

OVCAR-5 cells showed no increase in VEGF production when treated with 0.5 $\mu$M ce6 and 5 Jcm$^{-2}$; 0.5 $\mu$M ce6 and 20 Jcm$^{-2}$; 2 $\mu$M ce6 and 5 Jcm$^{-2}$; and 2 $\mu$M ce6 and 20 Jcm$^{-2}$. However, a decrease in VEGF production was observed in cells exposed to 2 $\mu$M ce6 and 20 Jcm$^{-2}$.

The two cell types that showed an increase in production of VEGF were keratinocyte cell lines. Keratinocytes have been reported to be a good source of VEGF for wound healing.

TABLE 1

| | VEGF Production | | | | | | | | | | | | |
|---|---|---|---|---|---|---|---|---|---|---|---|---|---|
| | Balb/mk | | | | OVCAR-5 | | | | PAM212 | | | | |
| pl-ce6-succ ($\mu$M) | 0 | 0.5 | 0.5 | 2 | 0 | 0.5 | 0.5 | 2 | 2 | 0 | 0.5 | 0.5 | 2 | 2 |
| light Jcm-2 | 0 | 5 | 20 | 5 | 0 | 5 | 20 | 5 | 20 | 0 | 5 | 20 | 5 | 20 |

TGF-$\beta$ secretion

A bioassay, as described by Nunes et al. ((1995) *J. Immunol. Methods* 186:267–274), was used to investigate whether cells increased their secretion of TGF-$\beta$ into the extracellular medium following administration of an effective dose of PDT. The bioassay determined TGF-β activity by measuring the ability of TGF-β to inhibit proliferation of epithelial cells. The cell line Mv1Lu, derived from lung epithelial cells of the mink was used because this cell line was known to be particularly susceptible to this effect. The ability of TGF-β to inhibit proliferation was quantified by measuring tritiated thymidine (3H-thymidine) uptake by the Mv1Lu cells.

To determine whether PDT caused target cells to actually synthesize more TGF-β, or to release existing intracellular stores of TGF-β, both Mv1Lu cell lysates and conditioned medium were tested for TGF-β bioactivity.

Various cell lines, i.e., J774, OVCAR-5, NB Rat, EA HY926 and PAM 212, were grown in P35 dishes to 80% confluency. The cells were then incubated with 2 μM pl-ce6-succ and pl-ce6 for 3 hours. Following incubation, the cells were washed with PBS and then illuminated with red light from the diode array for a fluence of 1 $cm^{-2}$ or 2 $cm^{-2}$ delivered at 12 $mWcm^{-2}$. The cells were then returned to the incubator for 24 hours whereupon the medium was aspirated, acidified, neutralized, and applied to Mv1Lu cells. The inhibition of 3H-thymidine uptake was compared to that produced by authentic TGF-β standards.

The cells, which were returned to the incubator for 24 hours, were then lysed by acidification, neutralized and added to Mv1Lu cells. The inhibition of 3H-thymidine uptake was compared to that produced by authentic TGF-β standards.

Table 2 below gives the percentage inhibition of 3H-thymidine uptake produced by the PDT conditioned medium. The acid/alkaline treated control cell conditioned media was used as the 100% value. Data presented represent at least duplicate results.

A significant increase in TGF-β secretion was observed in all cell lines that underwent PDT (Table 2). This indicated that PDT upregulated the secretion of TGF-β from cells.

The cell lysates did not produce any significant growth inhibition or stimulation under these conditions.

TABLE 2

Tritiated Thymidine Uptake

| Conjugate | pl-ce6-succ (% inhibition) | | pl-ce6 (% inhibition) | |
|---|---|---|---|---|
| Light dose | 1 $Jcm^{-2}$ | 2 $Jcm^{-2}$ | 1 $Jcm^{-2}$ | 2 $Jcm^{-2}$ |
| Cell Line | | | | |
| J774 | 35 | 50 | 43 | 50 |
| OVCAR-5 | 43 | 35 | 50 | 55 |
| NB Rat | 72 | 60 | | |
| EA HY926 | 20 | 31 | 52 | 53 |
| PAM 212 | 27 | 47 | 52 | 59 |

Intracellular Expression and Localization of TGF-β and VEGF

Immunochemical analysis was used to investigate whether PDT had an effect on the expression and localization of TGF-β and VEGF.

Cells (J774, OVCAR-5, NB rat keratinocyte, EA hy 926, and Pam 212) were grown on glass cover slips, incubated with conjugate and treated with light as described above. After 24 hours the cells were fixed with methanol, and reacted with rabbit monoclonal antibodies against TGF-β or VEGF. Then a second alkaline peroxidase conjugated goat anti-rabbit monoclonal antibody was applied. The staining was developed using the appropriate reagents and conventional techniques.

The intensity of the staining in both the plasma membrane and cytoplasm was assessed on a scale of 0–3, and the frequency with which of negative cells arose was determined. Cells were either untreated (control) or treated with pl-ce6 and pl-ce6-succ with and without the application of 2 $Jcm^{-2}$ light.

Table 3 summarizes data on TGF-β expression and localization in five cell types, in response to non-ablative PDT. The application of photoactivating light to the photosensitizer-treated cells affected both the expression and localization of TGF-β (Table 3). In some combinations, e.g., in the NB rat keratinocyte cells, the treatment of cells with light and the photosensitizer caused the number of negative cells to increase sharply (presumably because TGF-β was secreted into the medium). In other cells (OVCAR-5 or Ea.hy926 cell lines) there was an increase in the membrane or cytoplasmic staining.

TABLE 3

TGF-β Expression

| | plasma membrane | cytoplasm | negative |
|---|---|---|---|
| J774 cell line | | | |
| control | 3 | 1 | 0 |
| pl-ce6-succ dark | 1 | 3 | 0 |
| pl-ce6-succ 2$Jcm^{-2}$ | 1 | 3 | 0 |
| pl-ce6-dark | 2 | 3 | 0 |
| pl-ce6 2$Jcm^{-2}$ | 1 | 3 | 1 |
| OVCAR-5 cell line | | | |
| control | 2 | 2 | 1 |
| pl-ce6-succ dark | 1 | 2 | 0 |
| pl-ce6-succ 2$Jcm^{-2}$ | 2 | 2 | 1 |
| pl-ce6 dark | 2 | 2 | 0 |
| pl-ce6 2$Jcm^{-2}$ | 3 | 3 | 1 |
| NB rat keratinocyte cell line | | | |
| control | 2 | 2 | 2 |
| pl-ce6-succ dark | 1 | 0 | 0 |
| pl-ce6-succ 2$Jcm^{-2}$ | 1 | 1 | 3 |
| pl-ce6 dark | 2 | 1 | 0 |
| pl-ce6 2$Jcm^{-2}$ | 2 | 0 | 3 |
| EA.hy 926 cell line | | | |
| control | 3 | 1 | 0 |
| pl-ce6-succ dark | 1 | 3 | 0 |
| pl-ce6-succ 2$Jcm^{-2}$ | 1 | 2 | 2 |
| pl-ce6 dark | 2 | 2 | 2 |
| pl-ce6 2$Jcm^{-2}$ | 3 | 2 | 0 |
| PAM 212 cell line | | | |
| control | 3 | 1 | 0 |
| pl-ce6-succ dark | 1 | 3 | 0 |
| pl-ce6-succ 2$Jcm^{-2}$ | 1 | 3 | 0 |
| pl-ce6 dark | 3 | 2 | 0 |
| pl-ce6 2$Jcm^{-2}$ | 3 | 2 | 0 |

Table 4 summarizes data on VEGF expression and localization in five cell types, in response to non-ablative PDT. The effect of photoactivating light on the expression level and localization of VEGF (Table 4) was smaller than that found for TGF-β (Table 3).

TABLE 4

VEGF Expression

| | plasma membrane | cytoplasm | negative |
|---|---|---|---|
| J774 cell line | | | |
| control | 0 | 1 | 0 |
| pl-ce6-succ dark | 2 | 2 | 0 |
| pl-ce6-succ 2Jcm$^{-2}$ | 2 | 2 | 0 |
| pl-ce6-dark | 3 | 3 | 0 |
| pl-ce6 2Jcm$^{-2}$ | 3 | 3 | 0 |
| OVCAR-5 cell line | | | |
| control | 1 | 1 | 0 |
| pl-ce6-succ dark | 1 | 1 | 0 |
| pl-ce6-succ 2Jcm$^{-2}$ | 1 | 1 | 0 |
| pl-ce6 dark | 1 | 1 | 2 |
| pl-ce6 2Jcm$^{-2}$ | 1 | 1 | 2 |
| NB rat keratinocyte cell line | | | |
| control | 1 | 1 | 3 |
| pl-ce6-succ dark | 1 | 1 | 3 |
| pl-ce6-succ 2Jcm$^{-2}$ | 1 | 1 | 3 |
| pl-ce6 dark | 1 | 0 | 3 |
| pl-ce6 2Jcm$^{-2}$ | 1 | 0 | 3 |
| Ea.hy 926 cell line | | | |
| control | 2 | 3 | 0 |
| pl-ce6-succ dark | 3 | 3 | 0 |
| pl-ce6-succ 2Jcm$^{-2}$ | 3 | 3 | 0 |
| pl-ce6 dark | 2 | 2 | 0 |
| pl-ce6 2Jcm$^{-2}$ | 2 | 2 | 0 |
| PAM 212 cell line | | | |
| control | 3 | 1 | 0 |
| pl-ce6-succ dark | 1 | 0 | 0 |
| pl-ce6-succ 2Jcm$^{-2}$ | 1 | 0 | 0 |
| pl-ce6 dark | 3 | 1 | 0 |
| pl-ce6 2Jcm$^{-2}$ | 3 | 1 | 0 |

Wound Breaking Strength

Several reports have shown that the wound healing response in healthy experimental animals was so robust that it could not be accelerated (Beck et al. supra; Broadley et al. (1989) *Biotechnol. Ther.* 1:55–68). Therefore, in this experiment, the wound healing was suppressed so that an effect of PDT on wound healing could be evaluated.

Copenhagen rats were given a single dose of 6-alpha-methylprednisolone (40 mg/kg body weight, i.v. in tail vein), and 48 h later they were shaved and two longitudinal full-thickness incisions 3 cm long and down to the panniculus carnosus were made on the dorsum either side of the spine. Immediately following the wounding the incisions were closed with Michel clips. After 24 hours the conjugate pl-ce6-succ was injected into the tissue surrounding the wound. The dose was 0.2 mg pl-ce6-succ equivalent/kg body weight, and was administered in six 50 µl aliquots of phosphate buffered saline around the wound. Four hours later the entire wound and surrounding tissue was exposed to red light from a diode array centered on 670 nm. 2Jcm$^{-2}$ was delivered at a power density of 12 mW cm$^{-2}$. After five days the Michel clips were removed, and after a further two days the rats were sacrificed and the wounds excised. The wound breaking strength was measured on the fresh wound strips using a Chantillon TCD 200 tensiometer (Commercial Scale Co. Inc., Agawam, Mass.).

The wound breaking strength in control mice, i.e., mice that did not receive PDT (n=13), was 55.7 g±9.9 g. At least a three-fold increase in the wound strength, was observed in mice (n=13) that underwent PDT (187 g±26.8 g). These data indicated acceleration of wound healing in mice by the PDT.

Other embodiments are within the following claims.

We claim:

1. A method for accelerating the healing of a wound in a mammal, comprising:
   (a) identifying an unhealed wound site or partially-healed wound site in a mammal;
   (b) administering an effective amount of a photosensitizer to the mammal;
   (c) waiting for a time period wherein the photosensitizer reaches an effective tissue concentration at the wound site;
   (d) photoactivating the photosensitizer at the wound site by delivering specifically to the wound site light of an effective wavelength and intensity, for an effective duration, thereby producing an effective dose of photodynamic therapy;
   the dose of photodynamic therapy being sufficient to stimulate production of a growth factor by a cell at the wound site, without causing tissue destruction;
   thereby accelerating healing of the wound in the mammal.

2. The method of claim 1, wherein the growth factor is selected from the group consisting of PDGF, TGF-β, α-FGF, β-FGF, TGF-α, EGF, IGF, VEGF, KGF, and HGF.

3. The method of claim 1, wherein the cell at the wound site is selected from the group consisting of a fibroblast cell, a myofibroblast cell, a macrophage cell, an endothelial cell, and an epithelial cell.

4. The method of claim 1, wherein the photosensitizer is a macromolecular conjugate.

5. The method of claim 1, wherein the photosensitizer is selected from the group consisting of: a porphyrin, a chlorin, a bacteriochlorin, a purpurin, a phthalocyanine, a naphthalocyanine, a texaphyrin, and a non-tetrapyrrole photosensitizer, and conjugates thereof.

6. The method of claim 1, wherein the photosensitizer localizes to a particular cell type or to an organelle of a cell at the wound site.

7. The method of claim 1, wherein the photosensitizer is targeted to a particular cell type or to an organelle at the wound site by conjugation to a targeting moiety.

8. The method of claim 5, wherein the targeting moiety is selected from the group consisting of a polypeptide and a microparticle.

9. The method of claim 1, wherein the administration of the photosensitizer is systemic.

10. The method of claim 9, wherein the administration is between about 0.1 mg/kg and about 50 mg/kg.

11. The method of claim 10, wherein the administration is between about 0.5 mg/kg and about 10 mg/kg.

12. The method of claim 9, wherein the administration is parenteral.

13. The method of claim 1, wherein the administration of the photosensitizer is local.

14. The method of claim 13, wherein the administration is topical.

15. The method of claim 1, wherein the photoactivating step comprises delivering light by means of optical fibers.

16. The method of claim 1, wherein the photoactivating step comprises delivering light by means of transillumination.

17. The method of claim 1, wherein the photoactivating step comprises delivering laser light.

* * * * *

UNITED STATES PATENT AND TRADEMARK OFFICE
CERTIFICATE OF CORRECTION

PATENT NO. : 6,107,466
DATED : August 22, 2000
INVENTOR(S) : Hasan et al.

Page 1 of 1

It is certified that error appears in the above-identified patent and that said Letters Patent is hereby corrected as shown below:

Column 1,
Line 15, please insert the following paragraph before BACKGROUNG OF THE INVENTION:
-- FEDERALLY SPONSORED RESEARCH OR DEVELOPMENT
This invention was made with Government support under Grant No. DE-FG02-91ER61228 awarded by the U.S. Department of Energy. The Government has certain rights in this invention. --

Signed and Sealed this

Fourth Day of January, 2005

JON W. DUDAS
*Director of the United States Patent and Trademark Office*